United States Patent [19]

Huber

[11] 4,112,003
[45] Sep. 5, 1978

[54] PROCESS FOR PREPARING POLYPHENOLS

[75] Inventor: Ulrich Huber, Zurich, Switzerland

[73] Assignee: Givaudan Corporation, Clifton, N.J.

[21] Appl. No.: 765,495

[22] Filed: Feb. 3, 1977

[30] Foreign Application Priority Data

Feb. 12, 1976 [CH] Switzerland .................. 1709/76
Dec. 21, 1976 [CH] Switzerland .................. 16091/76

[51] Int. Cl.² ................................. C07C 41/00
[52] U.S. Cl. .................. 260/613 D; 260/389; 260/345.9 R; 568/805; 260/613 R
[58] Field of Search ............ 260/621 F, 613 D, 389, 260/345.9, 613 R

[56] References Cited

U.S. PATENT DOCUMENTS

| | | | |
|---|---|---|---|
| 2,632,025 | 3/1953 | Grob | 260/613 D X |
| 2,704,771 | 3/1955 | Smith | 260/613 D X |
| 3,904,695 | 9/1975 | Hendrickx et al. | 260/613 D |

Primary Examiner—Bernard Helfin
Attorney, Agent, or Firm—Thomas Cifelli, Jr.; Robert F. Tavares

[57] ABSTRACT

Polyphenols of the general formula:

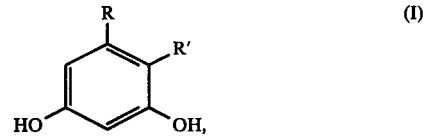

wherein R represents a readily cleavable ether group and R' represents a hydrogen atom or a lower alkoxycarbonyl, such as the methoxycarbonyl or ethoxycarbonyl group, and of phloroglucinol, are made by heating a compound of the general formula:

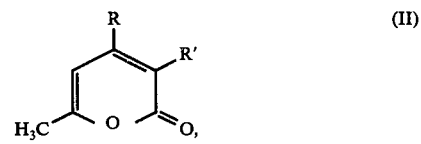

wherein R and R' have the same significance given above, with an alkali metal alcoholate and, if desired, converting the resulting compound of formula I into pholoroglucinol by ether-cleavage and removal of any ester group denoted by R' which may be present in accordance with methods known per se.

12 Claims, No Drawings

PROCESS FOR PREPARING POLYPHENOLS

FIELD OF THE INVENTION

This invention relates to the field of organic chemical synthesis.

DESCRIPTION OF THE PREFERRED EMBODIMENTS

Examples of readily cleavable ether groups denoted by R are lower alkoxy (e.g. methoxy, ethoxy and the like), cyclohexyloxy, benzyloxy, trityloxy, (lower alkoxy)-(lower alkoxy) (e.g. 2-methoxy-2-propoxy), 2-tetrahydropyranyloxy, propargyloxy and the like. The methoxy group is the preferred readily cleavable ether group.

The alkali metal alcoholates are conveniently derived from lower alkanols such as methanol, ethanol, isopropanol and tert.butanol, from (lower alkoxy)-lower alkanols such as ethoxyethyl alcohol or from benzyl alcohol. The preferred alkali metal alcoholates are alkali metal ethylates and isopropylates. The alkali metal is lithium, sodium or potassium, with lithium or sodium being preferred.

The aforementioned lower alkoxy groups and lower alkanols contain up to 7 carbon atoms.

The heating of a compound of formula II with an alkali metal alcoholate is expediently carried out at 80° C. to 200° C. A preferred temperature range is from 110° C. to 150° C.

The heating of a compound of formula II with an alkali metal alcoholate can be carried out in the presence or absence of a solvent. Examples of suitable solvents which may be used are inert solvents such as aliphatic hydrocarbons (e.g. ligroin, paraffins, terpene hydrocarbons and the like), aromatic hydrocarbons (e.g. benzene, toluene, xylene and the like), ethers (e.g. dioxan, tetrahydrofuran, dimethoxyethane and the like) and alcohols (e.g. ethanol and the like) are suitable. Toluene, xylene and isopropanol are the preferred solvents.

The heating of a compound of formula II with an alkali metal alcoholate is conveniently carried out under an inert gas atmosphere (e.g. under nitrogen or argon).

The molar ratio of compound of formula II to alkali metal alcoholate is conveniently from 2:5 to 1:5.

During the heating of a compound of formula II with an alkali metal alcoholate the ether group R can be replaced by the alcoholate group by a vinylogous reaction, above all if the alcoholate group is sterically small, that is to say, for example, when sodium methylate, sodium ethylate or the like is used as the alkali metal alcoholate.

The isolation of a compound of formula I from the mixture obtained after the heating of a compound of formula II with an alkali metal alcoholate can be carried out according to methods known per se; for example, by taking up the mixture in water, acidification and extraction with a solvent (e.g. chloroform or ether).

The conversion of a compound of formula I into phloroglucinol can be carried out according to methods known per se for acidic ether-cleavage; for example, by the action of hydrohalic acids [see A. Mc. Killup, Synth. Comm. 4 (1), 35 (1974)] or by heating with pyridine hydrochloride to 200° C. to 220° C. [see Prey, Chem. Ber. 74, 1219, 1222 (1941)].

An ester group denoted by R' which may be present in a compound of formula I can be completely cleaved off, where required, by heating for a short time in an alkaline medium such as by heating to 100° C. in 2-N sodium hydroxide [see, for example, Kirk-Othmer, Encycl. Chem. Technol. (2. Edit.) 16, 208 (1968)]. In many cases spontaneous cleavage of the ester group R' is observed under the alkaline reaction conditions.

The starting materials of formula II, insofar as they are not known, can be prepared according to methods known per se.

The following Examples illustrate the present invention:

EXAMPLE 1

(a) 5 g of triacetic acid δ-lactone methyl ether and 9.7 g of powdered sodium ethylate are suspended in 100 ml of xylene and the suspension is maintained at reflux temperature under a nitrogen atmosphere and with stirring for 3 hours. After cooling, the mixture is added to 200 ml of water and extracted with ether. The aqueous phase is acidified and extracted three times with methylene chloride. The combined methylene chloride phases are dried over sodium sulphate and concentrated. In this manner there are obtained 5.5 g of a semi-crystalline mass which contains phloroglucinol monoethyl ether (yield 79%) in addition to solvent residues. NMR; (DMSO, 60 MHz) 3.61/s 3H (OCH$_3$); 5.82/Sb 3 H (aromatic H); 9.2/Sb 2H (OH). The same results are obtained when naphthalene or cumene is used as the solvent in place of xylene and/or when lithium ethylate is used in place of sodium ethylate.

(b) 2 g of phloroglucinol monoethyl ether are stirred in 100 ml of concentrated hydrochloric acid (35%) at room temperature for 2 days. The mixture is then partially neutralised (pH 2-3) with aqueous sodium carbonate solution, the precipitated sodium chloride is filtered off and the filtrate is extracted with 150 ml of ether in a Kutscher-Steudel extractor for 18 hours. The ether extract is dried over sodium sulphate and concentrated, there being obtained 1.4 g to 1.55 g (86% to 95%) of phloroglucinol which has a melting point of 209°-210° C. after recrystallisation from water.

The triacetic acid δ-lactone methyl ether used as the starting material is prepared as follows:

144 g of triacetic acid lactone [N. Collie, J. Chem. Soc. 59, 607 (1891)] and 80 g of anhydrous sodium carbonate are suspended in 1.4 litres of acetone and the suspension, together with 144 g of dimethyl sulphate, is heated under reflux for 2 hours. The solution is cooled, filtered, extracted with 500 ml of acetone and then concentrated. The crystalline crude product obtained is recrystallised from 300 ml of water and dried in a vacuum. There are obtained 120 g (75%) of triacetic acid δ-lactone methyl ether of melting point 87°-88° C.

When the procedure described in the preceding paragraph is carried out using diethyl sulphate in place of dimethyl sulphate there is obtained triacetic acid δ-lactone ethyl ether.

EXAMPLE 2

3.2 g of sodium are dissolved at reflux temperature in 100 ml of isopropanol, this procedure requiring 2 hours. 5 g of triacetic acid δ-lactone methyl ether are then added. The solvent is distilled off and the solid residue is heated to 185° C. for a further 30 minutes. After cooling, the mass is taken up in 175 ml of water, acidified and extracted three times with 100 ml of ether each time. The combined and dried ether fractions are concentrated and give 5.9 g of a viscous oil which contains 77% of a mixture of phloroglucinol monomethyl ether and phloroglucinol monoisopropyl ether in the ratio of ca 1:1 (83% yield). The individual components are separated by chromatography on silica gel using benzene/5% ether.

The mixture of ethers obtained according to the preceding paragraph can be converted into phloroglucinol according to the procedure described in part (b) of Example 1.

The same mixture of ethers as obtained according to the first paragraph of this Example can be obtained when 11.4 g of sodium isopropylate and 5 g of triacetic acid δ-lactone methyl ether are suspended in 100 ml of tetrahydrofuran and the mass obtained after concentration is heated to 185° C. for 30 minutes.

EXAMPLE 3

8 g of sodium are dissolved in 100 ml of 2-ethoxyethanol and the mixture is concentrated under a high vacuum and dried at 140° C./0.04 Torr. 16.3 g (145 mmol) of the resulting sodium salt are suspended, together with 5 g (35.7 mmol) of triacetic acid δ-lactone methyl ether, in 100 ml of xylene and the suspension is maintained at reflux under a nitrogen atmosphere for 30 minutes. The mixture is cooled, extracted with 200 ml of water and the aqueous phase washed twice with ether. It is then acidified to pH 2 and extracted three times with methylene chloride. After concentration of the methylene chloride phases, there are obtained 3.9 g (78%) of phloroglucinol monomethyl ether. NMR: (DMSO, 60 MHz) 1.27/triplet 3H (J = 3.5 Hz) (ethyl group); 3.90/quat. 2H (J = 3.5 Hz) (oxymethylene); 5.84/Sb 3H (aromatic H); 9.2/Sb 2H (OH). The same results (yield 70%) are obtained when sodium benzylalcoholate is used in place of sodium 2-ethoxyethanolate.

The conversion of the aforementioned monomethyl ether into phloroglucinol is carried out in the same manner as described in part (b) of Example 1.

EXAMPLE 4

23.8 g of propargyl bromide are added dropwise while cooling to 10 g of triacetic acid lactone and 10 g of sodium carbonate in 120 ml of dimethyl sulphoxide and the mixture is then stirred at room temperature for 2 hours. The mixture is taken up in ether and washed three times with water. The flocculent precipitate is filtered off and the ether phase is dried over sodium sulphate and concentrated. The filtrate (4.7 g) and residue (6.1 g) are found to be pure triacetic acid lactone 3-O-propargyl ether; melting point 150°-151° C.; yield 83%.

In a manner analogous to that described in the preceding paragraph, triacetic acid lactone 3-O-benzyl ether (melting point 91.5°-92° C.) is obtained using benzyl bromide in place of propargyl bromide.

3 g of triacetic acid lactone 3-O-benzyl ether are suspended, together with 2.9 g (4 equivalents) of lithium ethylate, in 60 ml of cumene and the mixture is refluxed for 4 hours. The mixture is then worked-up according to the procedure described in part (a) of Example 1. There are obtained 1.5 g of viscous phloroglucinol monoethyl ether (71% of theory) which can be hydrolysed to give phloroglucinol according to the procedure described in part (b) of Example 1.

The conversion of the aforementioned propargyl ether into phloroglucinol can likewise be carried out according to the procedure described in part (b) of Example 1.

EXAMPLE 5

(a) 5 g of 2-carbethoxy-triacetic acid lactone (E. Suzuki, H. Sekizaki & S. Inone, Synthesis 1975, 652) are refluxed, together with 3.6 g of dimethylsulphate and 1.6 g of powdered potassium hydroxide, in 100 ml of acetone for 40 hours. The mixture is then filtered and concentrated. The residue in 20 ml of hot water is treated with active carbon and then extracted three times with 20 ml of chloroform each time. The chloroform extracts are combined and concentrated and the residue is recrystallised from methanol. There are obtained 2.7 g (51%) of the compound of formula II hereinbefore in which R represents the methoxy group and R' represents the carbethoxy group. This compound has a melting point of 137°-139° C.

(b) 1.1 g of sodium are dissolved in 5 ml of ethanol and the mixture is added to a solution of 2.5 g of the compound obtained according to paragraph (a) of this Example in 50 ml of ethanol. Ethanol is distilled off from the brown solution under normal pressure and the residue is heated to 185° C. for 30 minutes. The product is cooled, treated with 50 ml of water, washed twice with 20 ml of ether each time, acidified with 10% sulphuric acid and extracted three times with 50 ml of ether each time. The acidic ether fractions are dried over sodium sulphate and concentrated. There are obtained 1.2 g (65% of theory) of a brown oil, phloroglucinol monoethyl ether. This ether is converted into phloroglucinol in accordance with the procedure described in part (b) of Example 1.

When sodium tert.butylate in toluene is used in the procedure described in the preceding paragraph in place of sodium ethylate in ethanol there is obtained phloroglucinol monomethyl ether.

What is claimed is:

1. A process for the manufacture of compounds of the general formula

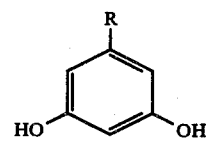

wherein R is lower alkoxy, cyclohexyloxy, benzyloxy, trityloxy, (lower alkoxy)-(lower alkoxy), 2 tetrahydropyranyloxy or propargyloxy, which comprises heating to 80° C. to 200° C. a compound of the general formula

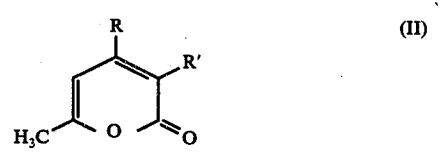

(II)

wherein R has the significance given earlier in this claim and R' represents a hydrogen atom or a lower alkoxycarbonyl group, with an alkali metal alcoholate, whereby the ratio of the compound of formula II to alkali metal alcoholate is 2:5 to 1:5, and cleaving off any lower alkoxycarbonyl group R', if still present, by heating the product

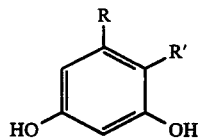

wherein R is as noted previously and $R_1$ is a lower alkoxycarbonyl to 100° C. in an alkaline medium.

2. A process according to claim 1, wherein the alkali metal alcoholate is derived from a lower alkanol, from benzyl alcohol or from a (lower alkoxy)-lower alkanol.

3. A process according to claim 1 for making phloroglucinol monethyl ether, which comprises heating triacetic acid delta-lactone methyl ether and sodium ethylate or lithium ethylate.

4. A process according to claim 1 for making a mixture of phloroglucinol monomethyl ether and phloroglucinol monoisopropyl ether, which comprises heating triacetic acid delta-lactone methyl ether and sodium isopropylate.

5. A process according to claim 1 for preparing phloroglucinol monomethyl ether, which comprises heating triacetic acid delta-lactone methyl ether and sodium 2-ethoxyethanolate or sodium benzyl/alcoholate.

6. A process according to claim 1 for preparing phloroglucinol monoethyl ether, which comprises heating triacetic acid lactone 3-O-benzyl ether and lithium ethylate.

7. A process according to claim 1 for preparing phloroglucinol monoethyl ether, which comprises heating a compound of formula II in which R represents the methoxy group and R' represents the carbethoxy group and sodium ethylate in the presence of ethanol.

8. A process according to claim 1 for preparing phloroglucinol monomethyl ether, which comprises heating

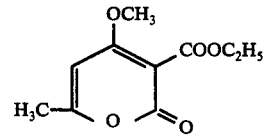

with sodium tert. butylate in the presence of toluene.

9. A process for preparing phloroglucinol, which comprises converting the compounds obtained in accordance with claim 1, into phloroglucinol by ether-cleavage.

10. A process in accordance with claim 9, wherein the compound of formula I is phloroglucinol monoethyl ether.

11. A process in accordance with claim 9, wherein the compound of formula I is a mixture of phloroglucinol monomethyl ether and phloroglucinol monoisopropyl ether.

12. A process in accordance with claim 9, wherein the compound of formula I is phloroglucinol monomethyl ether.

* * * * *